United States Patent [19]
Chance et al.

[11] Patent Number: 5,645,993
[45] Date of Patent: Jul. 8, 1997

[54] DELETION IN CHROMOSOME 17P11.2-12 WHICH CAUSES THE DISORDER HEREDITARY NEUROPATHY WITH LIABILITY TO PRESSURE PALSIES

[75] Inventors: Phillip F. Chance, Philadelphia, Pa.; Mary Kathryn Alderson; Shannon J. Odelberg, both of Salt Lake City, Utah; M. William Lensch, Devon, Pa.

[73] Assignee: University of Utah, Salt Lake City, Utah

[21] Appl. No.: 443,561

[22] Filed: May 18, 1995

Related U.S. Application Data

[63] Continuation of Ser. No. 122,971, Sep. 16, 1993, abandoned.

[51] Int. Cl.$^6$ .............................. C12Q 1/68; C12P 19/34; C07H 21/04; C12N 15/00

[52] U.S. Cl. .................. 435/6; 435/91.1; 435/810; 435/270; 536/23.1; 536/23.5; 536/24.31; 935/77; 935/78

[58] Field of Search ........................ 435/6, 91.1, 810, 435/270; 536/23.1, 23.5, 24.31; 935/77, 78

[56] References Cited

U.S. PATENT DOCUMENTS 5,306,616  4/1994  Lupski et al. .................. 435/6

OTHER PUBLICATIONS

Chance, et al., *Cell*, vol. 72, pp. 143–151, Jan. 15, 1993.

Sommer and Tautz, *Nucleic Acids Research*, vol. 17, No. 16, p. 6749, 1989.

Lewin, R., "When Does Homology Mean Something Else?", *Science*, vol. 237, Sep. 25, 1987, p. 1570.

Lebo et al., "Multicolor in Situ Hybridization and Linkage Analysis Order Charot–marie–Tooth Type 1 (CMT1A) Gene–Region markers," Am. J. Human Genet. 50:42–55 1992.

*Primary Examiner*—Bradley L. Sisson
*Attorney, Agent, or Firm*—Thorpe, North & Western, L.L.P.

[57] ABSTRACT

A method is disclosed for diagnosing Hereditary Neuropathy with Liability to Pressure Palsies (HNPP). A submicroscopic deletion of about 1.5 million basepairs on chromosome 17p11.2 is associated with the disorder in three unrelated pedigrees. The deletion includes all the markers known to map within the Charcot-Marie-Tooth type 1A (CMT1A) duplication. The method involves detecting the presence or absence of the deletion in DNA extracted from a patient sample. The deletion may be detected by Southern analysis or fluorescence in situ hybridization analysis (FISH). Sequences or probes that may be used to detect the deletion are provided, as are components of a kit for diagnosing HNPP.

19 Claims, 6 Drawing Sheets

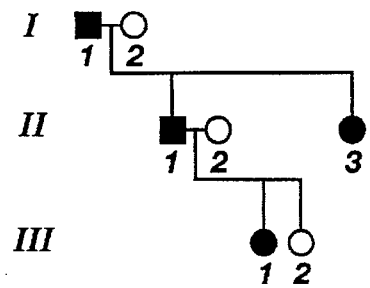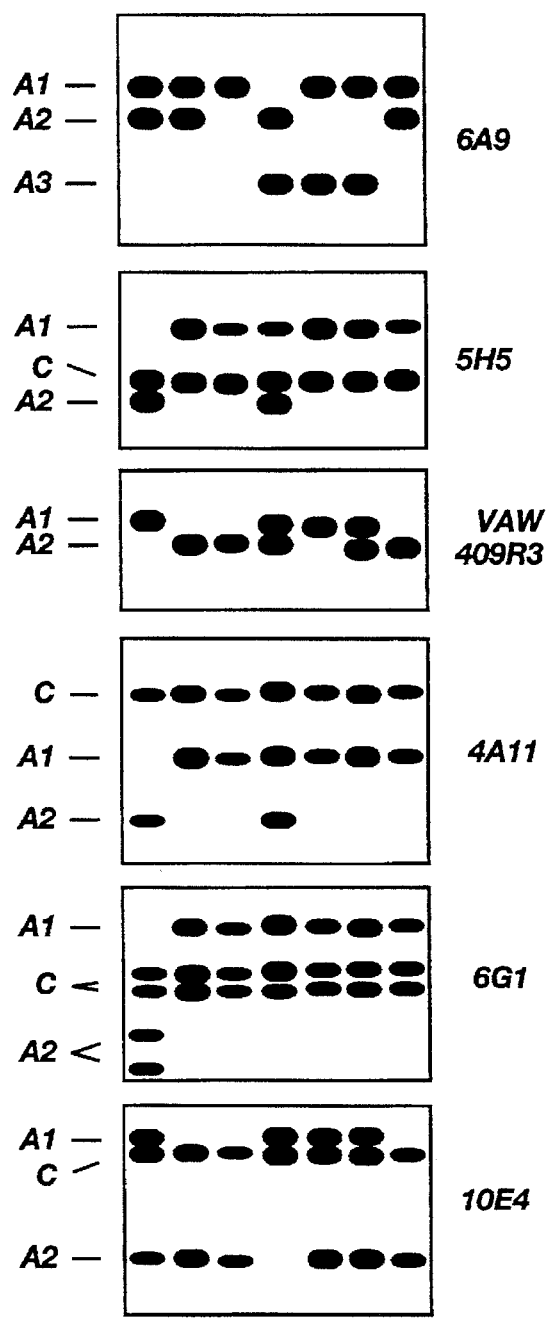
Fig. 3

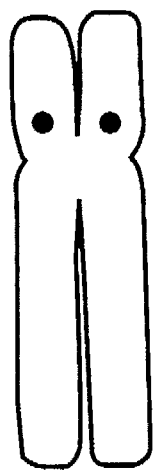 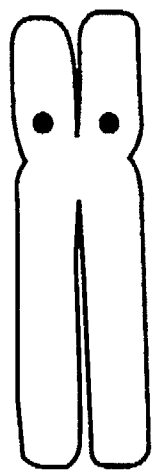 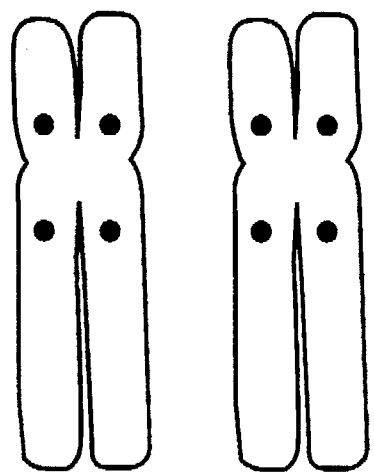
Fig. 4A                    Fig. 4B
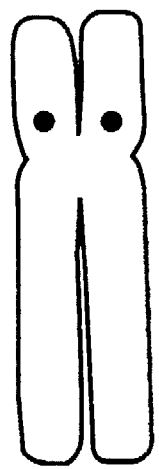 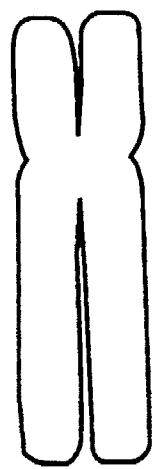 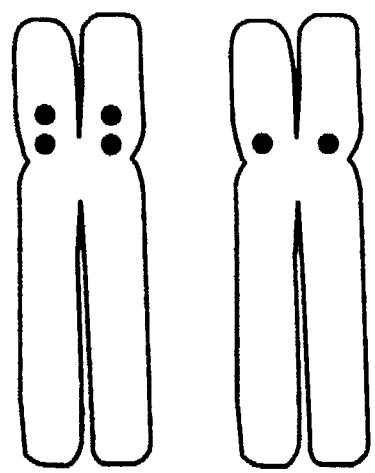
Fig. 4C                    Fig. 4D

DELETION IN CHROMOSOME 17P11.2-12 WHICH CAUSES THE DISORDER HEREDITARY NEUROPATHY WITH LIABILITY TO PRESSURE PALSIES

This application is a continuation of U.S. application Ser. No. 08/122,971 filed Sep. 16, 1993 of Philip Chance, et al., Abandoned, for DELETION IN CHROMOSOME 17p11.2-12 WHICH CAUSES THE DISORDER HEREDITARY NEUROPATHY WITH LIABILITY TO PRESSURE PALSIES.

BACKGROUND OF THE INVENTION

This invention relates to detection and diagnosis of disease in human subjects. More particularly, this invention relates to molecular diagnosis of the autosomal dominant disorder Hereditary Neuropathy with Liability to Pressure Palsies (HNPP) and to detection of the chromosomal deletion at the HNPP locus.

HNPP is an autosomal dominant disorder that causes episodes of focal demyelinating neuropathy following minor trauma to peripheral nerves. HNPP, also called familial recurrent polyneuropathy, tomaculous neuropathy, and McKusick Number 162500, typically has an onset during adolescence and may cause attacks of pain, muscular weakness, and atrophy. J. De Jong, 50 Psychiatr. Neurol. Bull. 60 (1947); D. Davies, 2 Lancet 266 (1954); C. Earl et al., 33 Quart. J. Med. 481 (1964); A. Staal et al., 15 Neurology 1008 (1965); A. Windebank, Inherited Recurrent Focal Neuropathies, Peripheral Neuropathy 1137-48 (3d ed. 1992).

Carpal tunnel syndrome and other entrapment neuropathies are frequent manifestations of this disorder. Motor and sensory nerve conduction velocities are sometimes mildly reduced in clinically affected patients and in asymptomatic gene carriers. P. Dyck et al., 10 Ann. Neurol. 222 (1981). Pathological changes observed in peripheral nerves of HNPP patients include segmental demyelination and tomaculous or sausage-like formations. F. Behse et al., 95 Brain 777 (1972); W. Bradley et al., 98 Brain 381 (1975); R. Madrid & W. Bradley, 25 J. Neurol. Sci. 415 (1975); J. Debruyne et al., 47 J. Neurol. Sci. 385 (1980).

Charcot-Marie-Tooth disease (CMT) is the most common inherited peripheral neuropathy in humans. Most patient pedigrees demonstrate an autosomal dominant Mendelian segregation pattern, although autosomal recessive and X-linked forms of CMT have been reported. For example, CMT loci have been mapped to chromosome 1 (CMT1B), T. Bird et al., 34 Am. J. Hum. Genet. 388 (1982), chromosome 17 (CMT1A), J. Vance et al., 104 Exp. Neurol. 186 (1989); J. Vance et al., 9 Genomics 623 (1991), another undetermined autosome (CMT1C), P. Chance et al., 47 Am. J. Hum. Genet. 915 (1990); P. Chance et al., 42 Neurology 2037 (1992), and the X chromosome, A. Gal. et al., 70 Hum. Genet. 38 (1985); K. Fishbeck et al., 20 Ann. Neurol. 527 (1986). CMT type 1A (CMT1A) appears to be the most prevalent form of the disease. CMT1A is associated with a submicroscopic DNA duplication spanning approximately 1.5 million bp of the short arm of chromosome 17, specifically at chromosome 17p11.2. J. Lupski et al., 66 Cell 219 (1991); P. Raemaekers et al., 1 Neuromusc. Dia. 93 (1991); P. Raemaekers et al., 29 J. Med. Genet. 5 (1992); J. Lupski et al., PCT WO 92/21694. Clinically, CMT results in a variably progressive atrophy of the distal muscles of the hands and feet. The muscular atrophy leads to an associated pes cavus foot and a claw hand deformity. The clinical signs and symptoms usually manifest themselves by the second or third decade of life, although electrophysiological abnormalities are evident much earlier. While CMT1A and HNPP are both classified as demyelinating peripheral neuropathies, their clinical and histopathological features are distinctly different.

A candidate gene for the CMT1A locus was identified when point mutations were found in the peripheral myelin protein 22 gene (Pmp-22) in mice containing the trembler (Tr) mutation and the related trembler-J (Tr$^J$). U. Suter et al., 356 Nature 241 (1992); U. Suter et al., 89 Proc. Nat'l Acad. Sci. USA 4382 (1992). The Tr mouse is a proposed model for CMT1A because the mutation results in a hypomyelinating neuropathy, is autosomally dominant, and maps to mouse chromosome 11, which has syntenic homology with human chromosome 17p in the region of the CMT1A locus. The human PMP-22 gene maps to chromosome 17p11.2 in the duplicated region associated with CMT1A and may be the critical gene associated with CMT1A. N. Matsunami et al., 1 Nature Genet. 176 (1992); P. Patel et al., 1 Nature Genet. 157 (1992); V. Timmerman et al., 1 Nature Genet. 171 (1992); L. Valentijn et al., 1 Nature Genet. 166 (1992). Gene dosage of the PMP-22 gene has been proposed as the causal factor of CMT1A.

Present methods of diagnosing HNPP are inadequate in that they are time consuming, expensive, painful, and risky to the patient. These methods include electrophysiological methods to measure nerve conduction velocities, histochemistry to quantitate nerve fibers in nerve biopsy material, and electron microscopy to examine the ultrastructure of involved nerves.

OBJECTS AND SUMMARY OF THE INVENTION

An object of the present invention is to provide a method for diagnosing HNPP that is rapid and inexpensive.

It is also an object of the invention to provide a method for diagnosing HNPP that is neither painful nor risky to the patient.

A further object of the invention is to provide oligonucleotides that may be used for diagnosing HNPP.

Still another object of the invention is to provide a method for detecting HNPP by measuring the presence or absence of a DNA deletion at a gene locus associated with HNPP.

Yet another object of the invention is to provide a kit for detecting HNPP wherein the kit includes a container and a probe to be used in Southern or fluorescence in situ hybridization (FISH) analysis for detecting the presence or absence of a deletion at the HNPP gene locus.

These and other objects may be accomplished by providing a method for detecting the presence or absence of a DNA deletion at the HNPP gene locus by extracting DNA from a sample to be tested and then subjecting the DNA to Southern analysis after having digested the DNA with a restriction endonuclease for which there is at least one site within the HNPP deletion region. The deletion may be detected by dosage measurements using methods including visual examination, densitometry, quantitative radioactivity, and quantitative fluorescence.

Another aspect of the invention involves providing a method for detecting the presence or absence of a DNA deletion at the HNPP gene locus by obtaining chromosomes from patient cells and determining marker dosage for markers within the HNPP deletion region by fluorescence in situ hybridization (FISH).

Still another aspect of the invention is providing a kit for detecting the presence or absence of a DNA deletion at the HNPP gene locus. The kit includes a container and an HNPP marker oligonucleotide for detecting the presence or absence of the marker in a patient sample by Southern or FISH analysis. Advantageously, a control marker oligonucleotide is provided also.

BRIEF DESCRIPTION OF THE DRAWINGS

FIG. 3 shows results of Southern blots demonstrating inheritance of chromosome 17p11.2 markers in the K1975 pedigree.

FIG. 4A shows results of fluorescence in situ hybridization (FISH) analysis of an HNPP proband using cosmid 5G7. FISH signals are represented by closed circles.

FIG. 4B shows results of fluorescence in situ hybridization (FISH) analysis of an HNPP proband using cosmid 10E4. FISH signals are represented by closed circles.

FIG. 4C shows results of fluorescence in situ hybridization (FISH) analysis of an HNPP proband using cosmid 6G1. FISH signals are represented by closed circles.

FIG. 4D shows results of fluorescence in situ hybridization (FISH) analysis of an HNPP proband using cosmid 5H5. FISH signals are represented by closed circles.

DETAILED DESCRIPTION OF THE INVENTION

Before the present method of diagnosing Hereditary Neuropathy with Liability to Pressure Palsies (HNPP) is disclosed and described, it is to be understood that this invention is not limited to the particular process steps and materials disclosed herein as such process steps and materials may, of course, vary. It is also to be understood that the terminology used herein is used for the purpose of describing particular embodiments only and is not intended to be limiting since the scope of the present invention will be limited only by the appended claims.

Identification of a Deletion in Chromosome 17p11.2 in HNPP

Figure 1A:
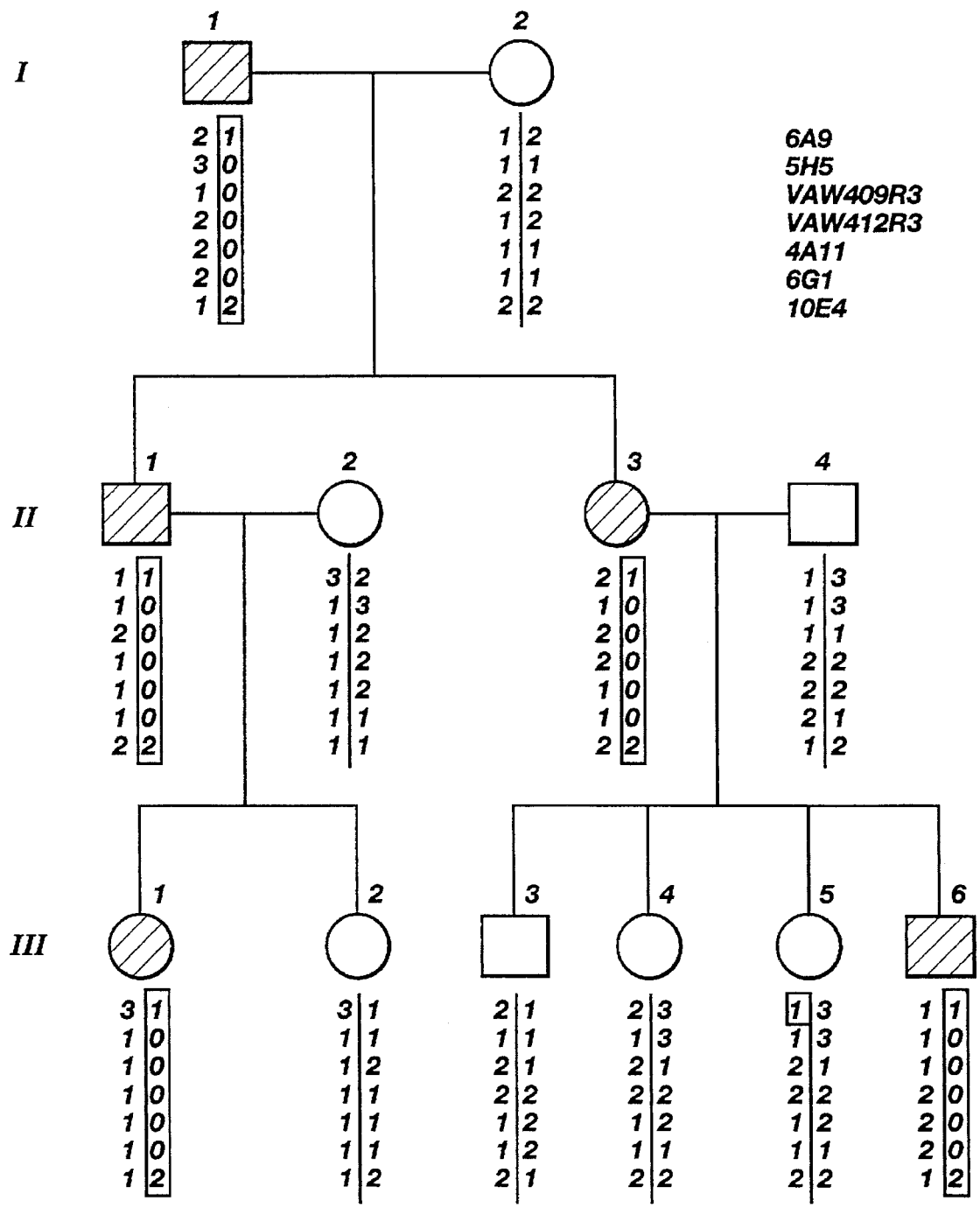
FIG. 1A shows pedigree K1975 segregating a mutant allele responsible for HNPP.
Figure 1B:
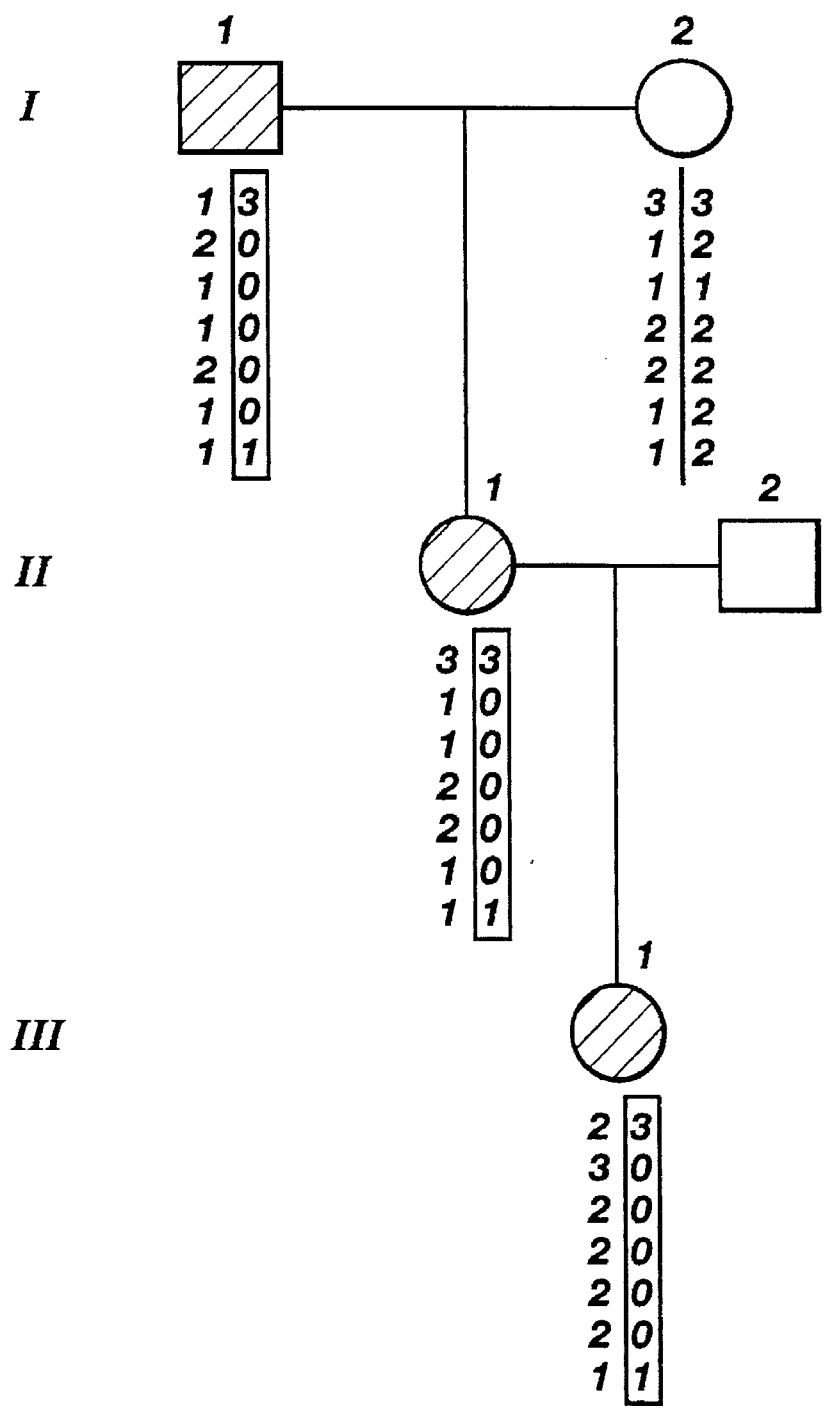
FIG. 1B shows pedigree K1903 segregating a mutant allele responsible for HNPP.
Figure 1C:
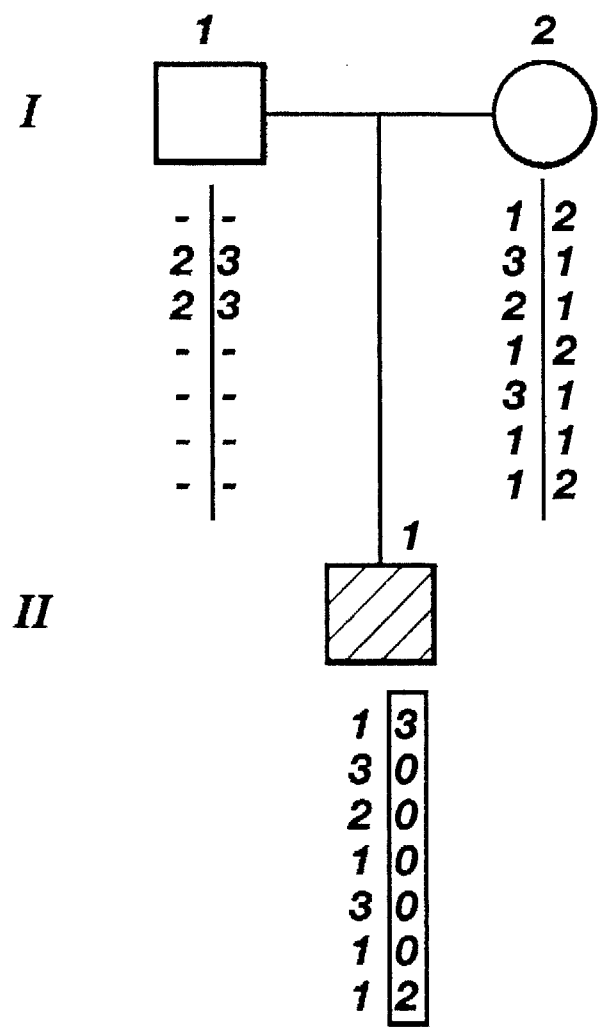
FIG. 1C shows pedigree K1942 segregating a mutant allele responsible for HNPP.

Three pedigrees (K1903, K1942, and K1975) segregating a mutant allele responsible for HNPP were studied. These pedigrees are shown in FIGS. 1A, 1B, and 1C, where affected persons are represented by closed symbols, males are shown as squares, and females as circles. A diagnosis of recurrent HNPP was established in probands and individuals at risk by a history of painful, prolonged palsies following mild trauma and characteristic neurophysiological findings. All persons in affected pedigrees K1903, K1942, and K1975 gave histories and had clinical examinations consistent with HNPP. The following specific neurophysiological findings were noted in affected persons:

(1) Mean median motor nerve distal latencies were 4.6 to 5.9 ms (normal, <4.5 ms);

(2) Normal segmental median motor nerve conduction velocities were >50 m/s;

(3) Prolonged median sensory peak conduction velocities ranged from 30 to 35 m/s (normal, >37 m/s);

(4) Prolonged radial sensory peak conduction velocities ranged from 31 to 36 m/s (normal, >38 m/s);

(5) Slowed sural nerve peak conduction velocity ranged from 24 to 28 m/s (normal, >36 m/s);

(6) Prolonged peroneal distal latencies were 7.4 to 8.9 ms (normal, <6.5 ms); and (7) Normal or slightly impaired peroneal motor nerve conduction velocities were 35–50 m/s (normal, >40 m/s).

Figure 2:
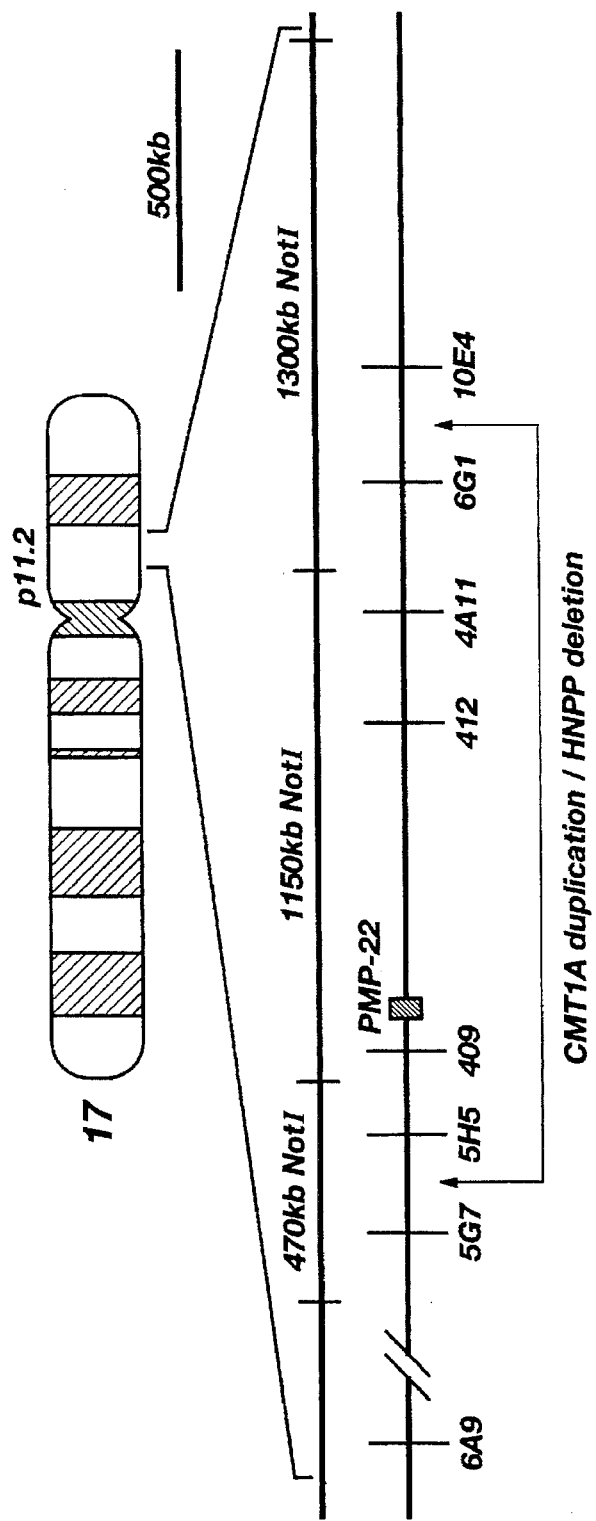
FIG. 2 shows a physical map of markers from chromosome 17p11.2.

The segregation patterns of eight DNA markers located in the CMT1A region of chromosome 17p11.2 were followed in these pedigrees. A physical map of these markers is given in FIG. 2. Markers mapping to the HNPP deletion and the CMT1A duplication are indicated, as are intervals containing the deletion and duplication breakpoints. Approximate physical distances are represented by NotI restriction fragments spanning the region.

High molecular weight DNA was isolated from peripheral blood or lymphoblasts by standard methods. Restriction enzyme digests were carried out according to the instructions of manufacturers. Gel electrophoresis and Southern transfer to nylon membranes (Hybond M, Amersham) were performed as described in P. Chance et al., 47 Am. J. Hum. Genet. 915 (1990), which is hereby incorporated by reference. Probes used were cosmids 6A9 (D17S456), 5G7 (D17S458), 5H5 (D17S455), VAW409R3 (D17S122) (ATCC accession no. 61477), 4A11 (D17S459), 6G1 (D17S457), and 10E4(D17S460), which were described in R. Lebo et al., 50 Am. J. Hum. Genet. 42 (1992); N. Matsunami et al., 1 Nature Genet. 176 (1992). Cosmids 5H5, 6A9, 4A11, 6G1, and 10E4 used for diagnosing HNPP were deposited on or before Jul. 12, 1994, with the following International Depository Authority: American Type Culture Collection, 12301 Parklawn Drive, Rockville, Md. 20852 USA. Probes were labeled with $^{32}$P to high specific activity ($5 \times 10^8$ to $5 \times 10^9$) by the random hexamer primer method of A. Feinberg & B. Vogelstein, 137 Anal. Biochem. 266 (1984). Hybridizations were carried out overnight at 65° C. in a solution containing 10% polyethylene glycol, 7% SDS, 1.5× SSPE (0.225M NaCl, 15 mM sodium phosphate, pH 7.4, 1.5 mM Na$_2$EDTA), and 5× Denhardt's reagent and washed to a stringency of 0.1× SSC, 0.1% SDS for 5–15 minutes. Filters were placed against X-ray film (XOMAT-AR, Kodak) overnight at –70° C. Gene copy number was determined by visual assessment of polymorphic alleles and corroborated by quantitation of band density and comparison with a control marker (neurofibromatosis (NF1) gene fragment) using a Phosphorimager (Molecular Dynamics). Alternatively, gene copy number may be determined by direct quantitation of radioactivity in bands, such as with a betascope analyzer. Gene copy number may also be determined by labeling probes with fluorescent, rather than radioactive, probes and quantitating fluorescence from appropriate bands.

Initially, five affected members of pedigree K1975 were found to have only a single copy of the VAW409R3 (D17S122) locus on the basis of dosage intensities on autoradiograms. This observation is confirmed by densitometric assessment and by comparison with the NF1 gene that maps to chromosome 17q11.2.

FIG. 3 shows Southern blots demonstrating inheritance of chromosome 17p11.2 markers in the K1975 pedigree. Lack of transmission of alleles at loci 5H5, VAW409R3, 4A11, and 6G1 are shown, whereas flanking loci 6A9 and 10E4 show normal segregation of alleles. Positions of polymorphic alleles (A1, A2, and A3) and constant fragments (C) are indicated. Allele sizes and restriction enzymes are as follows: 6A9 (TaqI), A1=6.5 kb, A2=5.9 kb, A3=4.8 kb; 5H5 (MspI), A1=11.4 kb, A2=8.0 kb (this is allele 3 in FIG. 1), C=8.4 kb; VAW409R3 (MspI), A1=2.8 kb, A2=2.7 kb; 4A11 (MspI), A1=7.0 kb, A2=5.8 kb; 6G1 (PvuII), A1=11.0 kb, A2=8.5/7.8 kb; 10E4 (BamHI), A1=7.0 kb, A2=6.0 kb.

Segregation analysis is shown in FIG. 3 for a portion of pedigree K1975 in which affected members failed to transmit a VAW409R3 allele to their affected offspring. For example, individual I-1 (an affected male) did not transmit a VAW409R3 allele to his affected son (II-1) or to his affected daughter (II-3). Similarly, only one copy of VAW409R3 was detected in HNPP individuals from pedigrees K1903 and K1942 (data not shown). Therefore, a deletion in the CMT1A region of chromosome 17p11.2 appeared to be associated with HNPP-affected individuals but not with unaffected individuals.

Characterization of a Deletion in Chromosome 17p11.2 in HNPP

To characterize the HNPP-associated deletion further, additional DNA markers known to map to the CMT1A gene region (see FIG. 2) were tested. In HNPP patients, markers VAW412R3 (ATCC accession no. 61483), 4A11, and 6G1, which are all distal to VAW409R3, were found to be present in only one copy by allele segregation or by dosage analysis. FIG. 3 shows an example in which individual I-1 of pedigree K1975 did not transmit a 4A11 or 6G1 allele to either of his affected offspring (II-1 and II-3). Similarly, marker 5H5, which lies proximal to VAW409R3 and is duplicated in CMT1A, is also deleted in HNPP. As shown in FIG. 3, individual I-1 did not transmit 5H5 to either of his affected offspring.

In contrast, marker 6A9, which has been physically mapped to a position proximal to VAW409R3, is neither duplicated in CMT1A (see FIG. 2) nor deleted in HNPP, as HNPP-affected individuals (e.g., I-1, II-3, and III-1 in K1975) demonstrated heterozygosity at this locus (FIG. 3). Therefore, the interval between 6A9 and 5H5 contains a proximal deletion breakpoint in HNPP and a proximal duplication breakpoint in CMT1A. Marker 10E4, which maps to a region distal to the CMT1A duplication, is not deleted in HNPP (FIG. 3). Two affected persons (I-1 and III-1 in K1975) are heterozygous at this locus, and affected individual II-1 transmitted an allele to his affected daughter (III-1). With 6G1 deleted and 10E4 present, the distal deletion breakpoint in HNPP is localized to the same interval as the CMT1A distal deletion breakpoint.

The deletion in HNPP and the duplication in CMT1A are estimated to be approximately $1.5 \times 10^6$ bp. The genotypes obtained with chromosome 17p11.2 markers in three HNPP pedigrees and segregation patterns of the deleted chromosome are summarized in FIGS. 1A, 1B, and 1C. Segregation patterns and genotypes for markers in chromosome 17p11.2 are given below each person studied. The markers, in order from top to bottom, are 6A9, 5H5, VAW409R3, VAW412R3, 4A11, 6G1, and 10E4. Haplotypes indicating the deleted chromosome are enclosed in boxes.

For pedigree K1942, the deletion appeared de novo in individual II-1 and is of paternal origin. The segregation analysis also detected a single recombinant in pedigree K1975, individual III-5, in whom a crossover had occurred between 6A9 and the deletion.

Paternity Analysis

Exclusion of paternity was examined as an explanation for the apparent lack of inheritance of 17p11.2 alleles in the segment of pedigree K1975 shown in FIG. 3. DNA (3 µg) from each individual was digested with HaeIII or HinfI and fractionated by electrophoresis through a 1.2% agarose gel. The DNA fragments were transferred in 0.4M NaOH to a nylon membrane by Southern blotting and were hybridized with probes labeled with $^{32}$P by the random hexamer priming method. Hybridizations were carried out at 65° C. in a buffer containing 2××SSPE (0.3M NaCl, 20 mM sodium phosphate, pH 7.4, and 2 mM Na$_2$EDTA), 7% SDS, and 250 µg/ml salmon sperm DNA. Probes pYNH24, pCMM101, and pEFD52 were hybridized to HaeIII-digested DNA samples and pYNZ22 was hybridized to HinfI digested DNA samples. Labeled molecular weight markers were used to identify 1 kb and 100 bp ladders. The blots were washed under high stringency and autoradiography was performed as described above. Allele sizes were determined by direct comparison with the molecular weight markers. Allele frequencies were obtained either from the Caucasian data base of the University of Utah DNA Paternity Testing Laboratory (for YNH24, CMM101, and EFD52) or from S. Odelberg et al., 5 Genomics 915 (1989) (for YNZ22). The paternity index and probability of paternity (assuming an a priori probability of 0.5) were calculated by standard methods.

With the four variable number of tandem repeat (VNTR) probes used in the paternity analysis, pYNH24 (D2S44), pCMM101 (D14S13), pEFD52 (D17S26), and pYNZ22 (D17S5), none demonstrated an exclusion of paternity. In all cases shown in this segment of pedigree K1975, the paternity index and probability of paternity were greater than 6,900:1 and 99.9%, respectively. Additionally, for pedigree K1942, in which the deletion is proposed to have occurred de novo, no exclusion of paternity or maternity was demonstrated with pYHN24 or pCMM101.

Fluorescence In Situ Hybridization (FISH)

To characterize the deletions in HNPP patients further, fluorescence in situ hybridization (FISH) was carried out using markers 6A9, 5G7, 5H5, 6G1, and 10E4. The procedure used was a modification of methods described previously by R. Moyzis et al., 95 Chromosoma 375 (1987); P. Smith et al., 5 Cancer 150 (1992). Metaphase chromosomes were prepared from lymphoblastoid cell lines. The cells were treated with colcemid (0.01 µg/ml) for 30 minutes before harvest and then with hypotonic solution (0.075M KCl). The chromosomes were fixed in methanol:acetic acid (3:1, v/v) and spread on glass slides. The slides were baked for 1 hour at 100° C., then treated with acetic anhydride, denatured in 70% formamide and 2× SSC for 3 minutes at 70° C., dehydrated, and air dried.

The probes used were cosmids (6A9, 5G7, 5H5, 6G1, and 10E4) biotinylated using the BioNick (Bethesda Research Laboratories, Gaithersburg, Md.) labeling system. Approximately 500 ng of probe and 30 µg of human COT1 DNA were used per slide. After denaturation at 75° C. for 5 minutes, the probes were preannealed for 6–8 hours at 37° C. before being placed on the slides. The probes were hybridized to the slide-bound chromosomes for 36–40 hours at 37° C. Posthybridization washes were performed for 15 minutes in 50% formamide and 4× SSC at 42° C.

Detection of the hybridization signals was performed using fluorescein-conjugated avidin (Vector Laboratories) that bound to the biotin-labeled nucleic acid probe. D. Pinkel et al., 83 Proc. Nat'l Acad. Sci. USA 2934 (1986). Signals were amplified by treatment with biotinylated goat anti-avidin (Vector Laboratories), followed by a second layer of fluoresceinated avidin. Slides were stained for 20 minutes with 7-aminoactinomycin D (Sigma, final concentration $5 \times 10^{-6}$M in McIlvain buffer (0.1M citric acid, 0.2M $Na_2HPO_4$), pH 7.5. They were then mounted in antifade (p-phenylene diamine, Sigma) containing 5 µg/ml Hoechst 33258 and 2 µg/ml propidium iodide. The slides were examined and photographed using a Zeiss fluorescence microscope equipped with epifluorescence and a double-band pass filter (Omega).

An average of 20–30 metaphase cells from each cell line were examined and scored after hybridization with each probe. Metaphase cells were scored only when both copies of chromosome 17 could be clearly identified. Interphase nuclei were examined after hybridization to cosmids 5H5 and 5G7, and the number of signals present in each nucleus was counted. At least 50 interphase nuclei were examined from each cell line.

These findings confirm that markers 6A9, 5G7, and 10E4 are not deleted in HNPP individuals. These markers hybridized to both homologs of chromosome 17 in nearly all metaphase cells examined from one HNPP proband in each pedigree (K1903, K1942, and K1975) with a pattern similar to a normal control individual. The results of hybridization with 5G7 are shown in FIG. 4A, wherein a FISH signal is present on both homologous chromosomes. In the case of marker 10E4, a second signal on the long arm of chromosome 17 was identified (FIG. 4B), which is consistent with previous observations, R. Lebo et al., 50 *Am. J. Hum. Genet.* 42 (1992), and suggests that this cosmid either is chimetic or detects a related sequence on the long arm.

Marker 6G1 hybridized to only one homolog of chromosome 17 in all metaphase cells examined from one proband of each of the three HNPP pedigrees (FIGS. 4C). When marker 6G1 was hybridized to chromosomes from a normal control cell line, signals on both chromosomes 17 were observed in each of 24 cells examined. Therefore, marker 6G1 is located physically within the region deleted in HNPP patients, which confirms the allele segregation analysis. Surprisingly, hybridization with marker 5H5, also shown to be deleted in HNPP by allele segregation analysis, demonstrated FISH signals on both homologs of chromosome 17 in almost every metaphase cell examined from the probands of the three pedigrees. However, one homolog consistently had a more intense signal than the other. The homolog with greater signal intensity often showed two distinct signals in close proximity to one another on the short arm (FIG. 4D). Analysis of each of the three lymphoblast cell lines from HNPP patients yielded approximately 80% of metaphase cells with unequal signals on the chromosome 17 homologs. In contrast, the normal control cell line showed only 33% of cells with minor differences in signal intensities on the homologs. These results with marker 5H5 result from 5H5 containing DNA identifying both a locus within the HNPP deletion and a locus more proximal on the short arm of chromosome 17 and mapping to the region harboring deletions responsible for the Smith-Magenis syndrome, F. Greenberg et al., 49 *Am. J. Hum. Genet.* 1207 (1991). Cosmid 5H5 may be chimeric, or it could contain a sequence with similarity to both regions on the short arm of chromosome 17.

The FISH analysis corroborated the observations of allele segregation analysis by confirming that markers 6G1 and 5H5, but not markers 6A9 and 10E4, are deleted in HNPP patients. Marker 5G7, which lies distally to marker 6A9, was shown to be present in HNPP by FISH analysis of metaphase chromosomes. This marker has not been followed by segregation analysis in HNPP or CMT1A owing to the absence of polymorphism among individuals tested. However, examination of Southern blots revealed no increase in hybridization intensity in CMT1A patients, suggesting that 5G7 is not part of the duplicated region. Furthermore, by FISH analysis 5G7 hybridized to interphase nuclei to yield two signals per nucleus in an average of 52% of nuclei from three CMT1A patients, in 52% of nuclei from one HNPP proband, and in 47% of nuclei from a normal control. This analysis confirmed that 5G7 lies proximally to the deletion in HNPP and the duplication in CMT1A. Therefore, the proximal breakpoint of the deletion in HNPP and the duplication in CMT1A must lie between markers 5G7 and 5H5.

Analysis of PMP-22 Gene in HNPP

Figure 5:
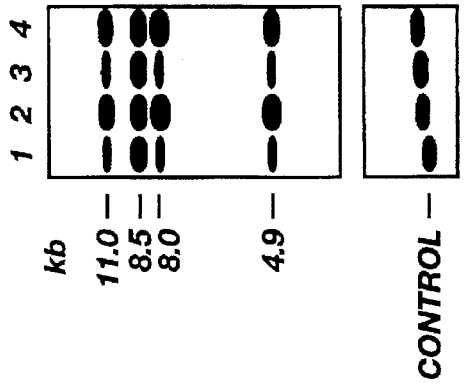
FIG. 5 shows results of a Southern blot demonstrating deletion of the PMP-22 gene from affected persons, but not from normal individuals, from the K1975 pedigree.

Gene dosage at the PMP-22 locus in HNPP was evaluated because of its implications as a candidate gene for CMT1A and its close map position (approximately 100 kb distal) to VAW409R3 in band 17p11.2. N. Matsunami et al., 1 *Nature Genet.* 176 (1992); P. Patel et al., 1 *Nature Genet.* 157 (1992); V. Timmerman et al., 1 *Nature Genet.* 171 (1992); L. Valentijn et al., 1 *Nature Genet.* 166 (1992). Genomic DNA (5 µg per person) was digested with Eco Ri, fractionated by gel electrophoresis, and blotted to a membrane. Hybridization was with a 480 bp probe synthesized by PCR, N. Matsunami et al., 1 *Nature Genet.* 176 (1992), from the published mouse Pmp-22 cDNA sequence, P. Spreyer et al., 10 *EMBO J.* 3661 (1991). As shown in FIG. 5, hybridization of a cDNA sequence for murine Pmp-22 to Eco RI-digested DNA detected four fragments in both normal (lanes 2 and 4) and affected (lanes 1 and 3) individuals. Three of these fragments (4.9, 8.0, and 11.0 kb) mapped to the 17p11.2 region, and each showed a decreased autoradiographic signal in all affected individuals relative to unaffected members of K1975, suggesting the presence of only a single copy of PMP-22 in HNPP. The 11.0 kb PMP-22 Eco RI fragment yielded a dosage ratio of 1.8:1.0 for normal persons and 1.0:1.0 for affected persons by comparison with the NF1 fragment. These densitometric ratios confirmed that one copy of PMP-22 is missing in affected persons from pedigree K1975. Similarly, only one copy of PMP-22 was detected in affected persons from pedigrees K1903 and K1942. Signal intensity of the fourth fragment (8.5 kb) shown in FIG. 5 was not diminished in HNPP patients. This fragment, which is not seen in yeast artificial chromosomes containing the PMP-22 gene represents either a separate gene with sequence similarity to PMP-22 or a pseudogene related to PMP-22.

Therefore, gene dosage of PMP-22 is a possible mechanism of HNPP. However, the possibility that one or more disrupted genes at deletion breakpoints has not been excluded. Also, it remains possible that the HNPP phenotype could be the result of monosomy for any of an estimated 20–30 other genes that map to the deleted region. The deleted region in HNPP likely contains other genes, the reduced expression of which might have adverse consequences, yet the only pathologic feature of HNPP appears to be a mild demyelinating neuropathy. These observations suggest that this region in distal 17p11.2 may contain only one gene that has its function significantly altered through reduced copy number.

Larger chromosomal deletions in band 17p11.2 are known to occur. Patients with Smith-Magenis syndrome have short stature, hypotonia, mental retardation with facial abnormalities, and cytogenetically detectable deletions of chromosome 17p11.2. A. Smith et al., 34 *Am. J. Hum. Genet.*

(Supp.) A410 (1982). Molecular characterization of DNA from a series of patients with this syndrome has shown that multiple DNA markers that map to proximal 17p11.2 are deleted. F. Greenberg et al., 49 Am. J. Hum. Genet. 1207 (1991). The Smith-Magenis syndrome region and the CMT1A duplication appear to involve adjacent segments of chromosome 17p11.2. Marker VAW409R3, which maps to the proximal portion of the CMT1A duplication, is not deleted in 30 of 31 Smith Magenis syndrome patients, suggesting that the CMT1A duplication is distal to the Smith-Magenis region. One Smith-Magenis syndrome patient whose deletion extended distally through markers duplicated in CMT1A (VAW409R3 and VAW412R3) was described as having no clinical signs of neuropathy. As the deletion would encompass the PMP-22 locus, a reexamination at an older age or careful evaluation with electrophysiological methods may detect evidence for HNPP.

Kit for Detecting HNPP

A kit for detecting HNPP is furnished by supplying a container in which are provided polynucleotide probes for detecting the presence or absence of the deletion associated with HNPP. Appropriate containers could be constructed of plastic, cardboard, or other suitable materials and should be large enough to hold as many 1 ml microfuge tubes as needed to supply the probes. Probes for detecting the HNPP deletion are preferably selected from 5H5, VAW409R3, PMP-22, VAW412R3, 4A11, and 6G1, although other probes within the HNPP deletion region would also be suitable. However, as discussed above, 5H5 is not preferred since it hybridizes to a site on chromosome 17 outside the HNPP deletion region as well as to a site within the deletion region. One or more control probes should be included with the kit also. Suitable control probes could include 6A9, 5G7, 10E4, and NF1, although other probes from outside the HNPP deletion region of chromosome 17 may work as well. Cosmid 10E4 is not preferred because it hybridizes to multiple sites on chromosome 17. The supplied HNPP-associated probe and control probe could be used to detect the HNPP deletion by Southern hybridization or FISH analysis, as well as in conjunction with other similar techniques.

The kit would be used by first obtaining a sample of blood from a patient to be tested. If Southern analysis were to be used to test for the presence or absence of the HNPP deletion, DNA would be isolated from peripheral blood or lymphoblasts by standard methods. Then, an appropriate quantity of the DNA, generally in the range of 1–5 µg, would be digested with a restriction endonuclease, fractionated by electrophoresis, and transferred to a membrane, as described above. Multiple membranes could be prepared for separate hybridization with HNPP and control probes, or a single membrane could be hybridized sequentially with HNPP and control probes with stripping of the bound signal between hybridizations. Depending on the control marker used, HNPP and control probes could be mixed to detect HNPP and control markers on the same membrane. Probe DNA would be labeled as described above. Then the membrane or membranes would be exposed to labeled probe DNA, washed to remove unbound probe, and imaged, as described previously. Then, the dosage difference, if any, of HNPP and control markers would be determined by visual examination or densitometry of an X-ray film.

The kit could also be used for FISH analysis of a patient's chromosomes, as described above. An appropriate cell sample would be obtained from the patient to be tested. The cells would be lysed, fixed, and spread on glass slides. HNPP and control probes would be labeled. Slide-bound chromosomes would be hybridized to the labeled probes and washed. Hybridization signals are developed and the slides stained, followed by examination by fluorescence microscopy.

We claim:

1. A method for diagnosing Hereditary Neuropathy with Liability to Pressure Palsies (HNPP) in an individual with symptoms thereof and for diagnosing a predisposition to HNPP in an individual prior to onset of symptoms thereof from a sample containing DNA from the individual to be tested comprising the step of detecting in the sample the presence or absence of a DNA deletion at a gene locus associated with HNPP.

2. The method of claim 1 wherein the deletion is determined by dosage differences of alleles measured by Southern analysis of restriction endonuclease digest using a probe that hybridizes to the deleted region of the HNPP locus.

3. The method of claim 2 wherein the probe is selected from the group consisting of 5H5, VAW409R3, VAW412R3, 4A11, and 6G1.

4. The method of claim 2 wherein the probe is PMP-22 probe.

5. The method of claim 2 wherein the dosage difference is measured by a method selected from the group consisting of visual examination, densitometry, quantitative radioactivity, and quantitative fluorescence.

6. The method of claim 5 wherein the dosage difference is measured by visual examination.

7. The method of claim 5 wherein the dosage difference is measured by densitometry.

8. The method of claim 1 wherein the deletion is detected by fluorescence in situ hybridization (FISH) using a probe that hybridizes to the deleted region of the HNPP locus.

9. The method of claim 8 wherein the probe is selected from the group consisting of 5H5, VAW409R3, VAW412R3, 4A11, and 6G1.

10. The method of claim 8 wherein the probe is PMP-22 probe.

11. A method for diagnosing Hereditary Neuropathy with Liability to Pressure Palsies (HNPP) in an individual with symptoms thereof and for diagnosing a predisposition to HNPP in an individual prior to onset of symptoms thereof from a sample containing DNA from the individual to be tested comprising the step of detecting in the sample a DNA deletion at a gene locus associated with HNPP, wherein the presence of said deletion is determined by a dosage of one-half that of a normal individual of an allele at said locus measured using a probe that hybridizes to said allele, wherein said probe is a member selected from the group consisting of 5H5, 4A11, and 6G1.

12. The method of claim 11 wherein said probe is 5H5.

13. The method of claim 11 wherein said probe is 4A11.

14. The method of claim 11 wherein said probe is 6G1.

15. A method for diagnosing Hereditary Neuropathy with Liability to Pressure Palsies (HNPP) in an individual with symptoms thereof and for diagnosing a predisposition to HNPP in an individual prior to onset of symptoms thereof from a sample containing DNA from the individual to be tested comprising the step of detecting in the sample a DNA deletion at a gene locus associated with HNPP, wherein the presence of said deletion is determined by a dosage of one-half that of a normal individual of an allele at said locus measured using a probe that hybridizes to said allele, wherein said probe is a member selected from the group consisting of VAW409R3, PMP-22, probe and VAW412R3.

16. The method of claim 15 wherein said probe is VAWR409R3.

17. The method of claim 15 wherein said probe is PMP-22 probe.

18. The method of claim 15 wherein said probe is VAW412R3.

19. A method for diagnosing Hereditary Neuropathy with Liability to Pressure Palsies (HNPP) in an individual with symptoms thereof and for diagnosing a predisposition to HNPP in an individual prior to onset of symptoms thereof from a sample containing DNA from the individual to be tested comprising the step of detecting in the sample a DNA deletion at a gene locus associated with HNPP, wherein the presence of said deletion is determined by a dosage of one-half that of a normal individual of an allele at said locus measured using a probe that hybridizes to said allele, wherein said probe is a member selected from the group consisting of 5H5, VAW409R3, PMP-22, probe VAW412R3, 4A11, 6G1, and fragments thereof.

* * * * *